United States Patent
Baade et al.

(10) Patent No.: US 9,907,965 B2
(45) Date of Patent: Mar. 6, 2018

(54) IMPLANTABLE MEDICAL DEVICES WITH HEADER STRUCTURES INCLUDING CONDUCTIVE PATHS THAT FACILITATE THE INTERCONNECTION OF FEEDTHROUGH CONDUCTORS TO ELECTRICAL CONNECTORS

(71) Applicant: MEDTRONIC, INC., Minneapolis, MN (US)

(72) Inventors: Michael J. Baade, Ramsey, MN (US); Katherine J. Bach, Arden Hills, MN (US); Steven T. Deininger, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 14/983,519

(22) Filed: Dec. 29, 2015

(65) Prior Publication Data
US 2016/0184594 A1 Jun. 30, 2016

Related U.S. Application Data

(60) Provisional application No. 62/098,251, filed on Dec. 30, 2014.

(51) Int. Cl.
*A61N 1/37* (2006.01)
*A61N 1/375* (2006.01)

(52) U.S. Cl.
CPC .......... *A61N 1/3754* (2013.01); *A61N 1/3752* (2013.01)

(58) Field of Classification Search
CPC ........................... A61N 1/3754; A61N 1/3752
USPC ......................................... 607/37
See application file for complete search history.

(56) References Cited

U.S. PATENT DOCUMENTS 8,233,986 B2 7/2012 Deininger et al.
9,138,588 B2 * 9/2015 Deininger ............ A61N 1/3754

* cited by examiner

*Primary Examiner* — Paula J Stice
(74) *Attorney, Agent, or Firm* — Withers & Keys, LLC

(57) ABSTRACT

Implantable medical devices include header structures with conductive paths from the feedthrough conductors that may be located on one side of the device to electrical connectors that may be located on an opposite side of the device. The conductive paths may include conductive interconnect pins and lead frame conductors. The conductive interconnect pins may be located in holes present in a header body where the conductive interconnect pins are attached to the feedthrough conductors on one end and are attached to the lead frame conductors on the opposite end. The lead frame conductors then extend to the corresponding electrical connectors. The header body may provide cavities on each side to allow for the insertion of stack assemblies that include the electrical connectors and lead frame conductors.

7 Claims, 14 Drawing Sheets

IMPLANTABLE MEDICAL DEVICES WITH HEADER STRUCTURES INCLUDING CONDUCTIVE PATHS THAT FACILITATE THE INTERCONNECTION OF FEEDTHROUGH CONDUCTORS TO ELECTRICAL CONNECTORS

TECHNICAL FIELD

Embodiments relate to implantable medical devices that include header structures that receive feedthrough conductors and contain electrical connectors. More particularly, embodiments relate to header structures that include conductive pathways that establish an interconnection between the feedthrough conductors and the electrical connectors.

BACKGROUND

Implantable medical devices provide a medical function such as electrical stimulation and/or physiological sensing. To provide the medical function, the implantable medical device includes electrical circuitry contained within a housing. In many implantable medical device designs, feedthrough conductors exit the housing and pass into a header structure mounted to the housing. The header structure includes one or more bores where electrical connectors are present and electrical signals are routed between the feedthrough conductors and the electrical connectors.

Medical leads or lead extensions have proximal ends that are positioned within corresponding bores of the header structure. The medical leads or lead extensions include proximal contacts that make electrical connection with the electrical connectors of the header structure. Conductors within an insulative lead body of the medical lead routes electrical signals between the electrical contacts and electrodes at the distal end of the lead body. The electrodes are positioned at a target site within the body by routing the lead between the implantation site of the implantable medical device and the target site. Electrical signals may then be passed between the electrical circuitry within the housing of the implantable medical device and the electrodes at the target site.

Typically, a set of pre-shaped lead frame conductors establish an interconnection of the feedthrough conductors to the electrical connectors. In some cases, individual conductors are manually routed from the feedthrough to the electrical connector by bending the conductor as may be necessary to achieve the proper route during construction of the header structure. In either case, problems may arise during manufacturing of the header structure, especially where the feedthrough conductors enter the header structure on one side while the electrical connectors are present on the opposite side, such as for a header structure that has laterally spaced bores. The relatively small size of the header structure and the components within the header structure makes successfully routing individual conductor wires without creating short circuits between adjacent conductors very difficult. Likewise, routing a lead frame conductor from one side of the header structure to another is troublesome as the lead frame has a pre-shaped configuration with bends that makes the manual routing awkward if not impossible.

SUMMARY

Embodiments address issues such as these and others by providing implantable medical devices with header structures that include conductive paths that facilitate the interconnection of the feedthrough conductors to the electrical conductors. For instance, the conductive path may be constructed of conductive pins that are attached to the feedthrough conductors on one end and inserted into holes that pass from one side of the header structure to the other, where lead frame conductors may then attach to the opposite end. Additionally, the lead frame conductors may interconnect the conductive pins to the electrical conductors by merely traveling in a relatively direct path, for instance in a vertical path relative to a horizontal lead bore, from the end of the conductive pin to the electrical connector on the same side of the header structure. Also, the header structure may utilize a header body that has an open cavity for each bore, where the lead frame conductors on the side opposite the feedthrough conductors may be positioned by being introduced into the open cavity on that side of the header body. The conductive pins may have features to ease installation, such as a shoulder that engages a corresponding shoulder within the hole of the header body.

Embodiments provide an implantable medical device that includes a housing and circuitry within the housing, the circuitry providing a plurality of feedthrough conductors that exit the housing. The implantable medical device further includes a header structure having a plurality of holes passing from a first side of the header structure to a second side of the header structure and a plurality of conductive pins, with a conductive pin on the plurality present within a corresponding hole of the plurality of holes. The conductive pin has a first end present on the first side of the header structure and a second end present on a second side of the header structure, the second end being electrically coupled to a corresponding feedthrough conductor. The implantable medical device further includes electrical connectors present within an interior of the header structure and a first set of lead frame conductors with each lead frame conductor of the first set being electrically coupled to the first end of a corresponding conductive pin present within one of the holes and being electrically coupled to a corresponding electrical connector within the header structure.

Embodiments provide a method of constructing an implantable medical device that involves providing a header body having a first cavity exposed on a first side of the header body, having a second cavity exposed on a second side of the header body, and having at least one hole extending from the first side to the second side, the first cavity being laterally spaced from the second cavity. The method further involves providing a first stack assembly within the first cavity, the first stack assembly comprising at least one electrical connector and a lead frame conductor electrically connected to the at least one electrical connector and providing a housing that houses electrical circuitry, the electrical circuitry providing feedthrough conductors that exit from the housing. The method additionally involves inserting a conductive pin into the hole and establishing an electrical connection between the lead frame conductor of the first side and a first end of the conductive pin present on the first side. The method also involves mounting the header body to the housing and establishing an electrical connection of a first feedthrough conductor to a second end of the conductive pin present on the second side.

Embodiments provide an implantable medical device that includes a housing, circuitry within the housing, the circuitry providing a plurality of feedthrough conductors that exit the housing, and a header structure having a plurality of holes passing from a first side of the header structure to a second side of the header structure. The implantable medical device further includes a plurality of conductive paths, with a conductive path of the plurality passing through a corresponding hole of the plurality of holes, the conductive path having a first end present on the first side of the header structure and a second end present on a second side of the header structure, the second end being electrically coupled to a corresponding feedthrough conductor. The implantable medical device also includes electrical connectors present within an interior of the header structure, wherein the header structure comprises a header body with a first cavity exposed to the first side of the header structure and a second cavity exposed to the second side of the header structure, with a first set of the electrical connectors being present within the first cavity and with a second set of the electrical connectors being present within the second cavity. The first end of each conductive path is electrically coupled to a corresponding electrical connector within the header structure.

Embodiments provide an implantable medical device that includes a housing, circuitry within the housing, the circuitry providing a plurality of feedthrough conductors that exit the housing, and a header structure having a plurality of holes passing from a first side of the header structure to a second side of the header structure. The implantable medical device further includes a plurality of conductive paths, with a conductive path of the plurality passing through a corresponding hole of the plurality of holes, the conductive path having a first end present on the first side of the header structure and a second end present on a second side of the header structure with the second end being electrically coupled to a corresponding feedthrough conductor. Each hole of the plurality of holes of the header structure defines a shoulder, wherein each of the conductive paths includes a portion that defines a shoulder, and wherein the shoulder of each conductive path engages the shoulder of a corresponding hole of the plurality of holes. Electrical connectors are present within an interior of the header structure and electrically coupled to corresponding conductive paths.

Embodiments provide an implantable medical device that includes a housing, circuitry within the housing, the circuitry providing a plurality of feedthrough conductors that exit the housing, and a header structure having a plurality of holes passing from a first side of the header structure to a second side of the header structure. The implantable medical device further includes a plurality of conductive paths, with a conductive path of the plurality passing through a corresponding hole of the plurality of holes, the conductive path having a first end present on the first side of the header structure and a second end present on a second side of the header structure, the second end being electrically coupled to a corresponding feedthrough conductor. A portion of each conductive path travels in a vertical direction from the corresponding hole to the corresponding electrical connector, with each hole being aligned along a horizontal direction with a corresponding electrical connector. Electrical connectors are present within an interior of the header structure and electrically coupled to corresponding conductive paths.

DETAILED DESCRIPTION

Embodiments provide conductive pathways that facilitate the interconnection of feedthroughs to electrical connectors within a header structure of an implantable medical device. The embodiments provide various features such as conductive pins that are inserted into holes that pass from one side of the header structure where feedthrough conductors are located to another side of the header structure where electrical connectors are located. The conductive pins and holes of the header structure may provide features to aid installation of the conductive pins such as a shoulder on the pin that engages a shoulder within the hole. The embodiments provide features such as a header body of the header structure where the header body has a cavity exposed to the corresponding side of the header body which allows stack assemblies that include electrical connectors, seals, set screw blocks, and the like to be positioned within the cavity. Embodiments also provide features such as lead frame conductors that extend vertically, relative to a horizontal bore defined by the electrical connectors within the cavity of the header body, from the conductor pin to the electrical connector, where the hole that contains the conductor pin is aligned in the horizontal direction relative to the corresponding electrical connector.

Figure 1:
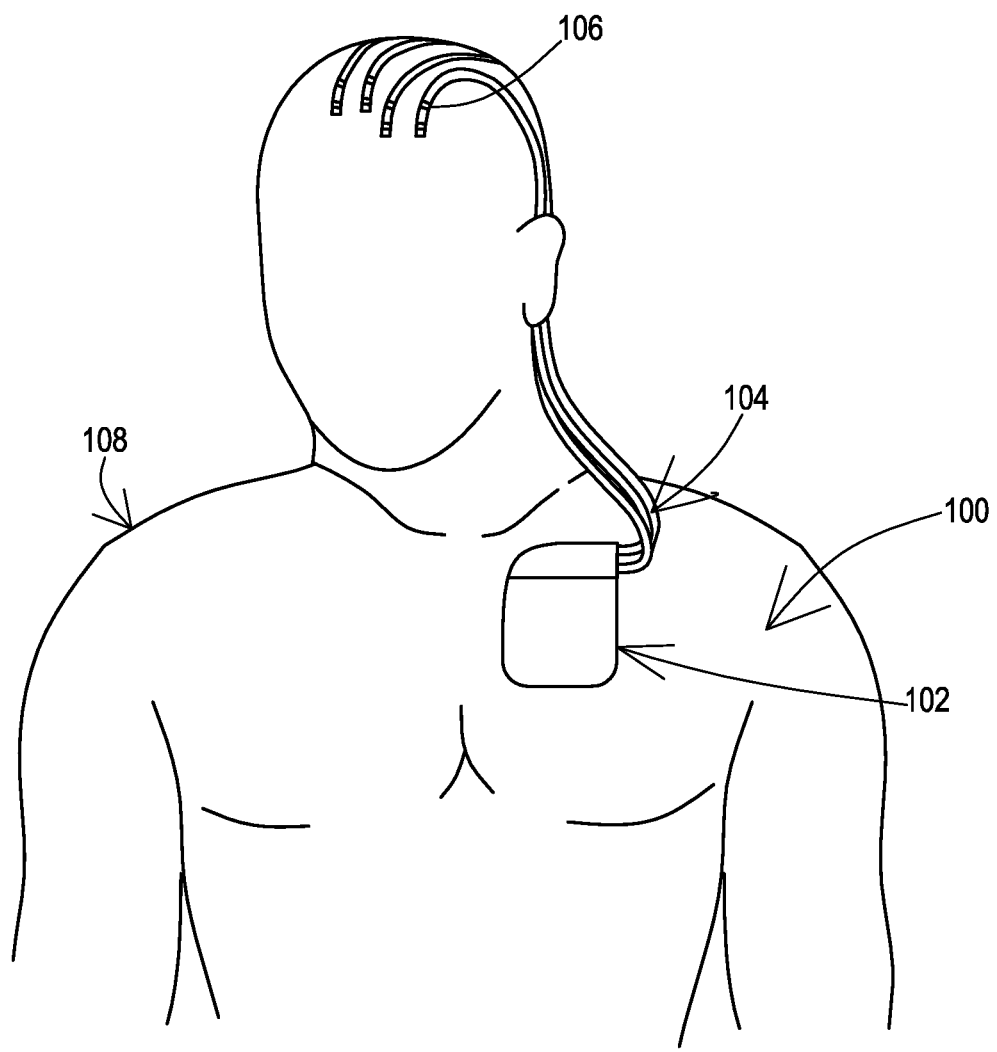
FIG. 1 shows an operating environment for various embodiments of the implantable medical device.

FIG. 1 shows an example of an implantable medical system 100 that includes an implantable medical device 102 and associated medical leads 104, which may also be a lead extension between the lead 104 and device 102 for situations where the lead 104 is not long enough to span the entire distance, that are implanted in a patient 108. In this example, the implantable medical system 100 is situated within the patient 108 to provide deep brain stimulation and/or sensing by having the medical leads 104 extend into the brain where distal electrodes 106 are positioned at a target site. However, it will be appreciated that aspects of the various medical device embodiments disclosed herein may be used for other purposes including other neurological purposes like spinal cord stimulation and also cardiac purposes.

Figure 2:
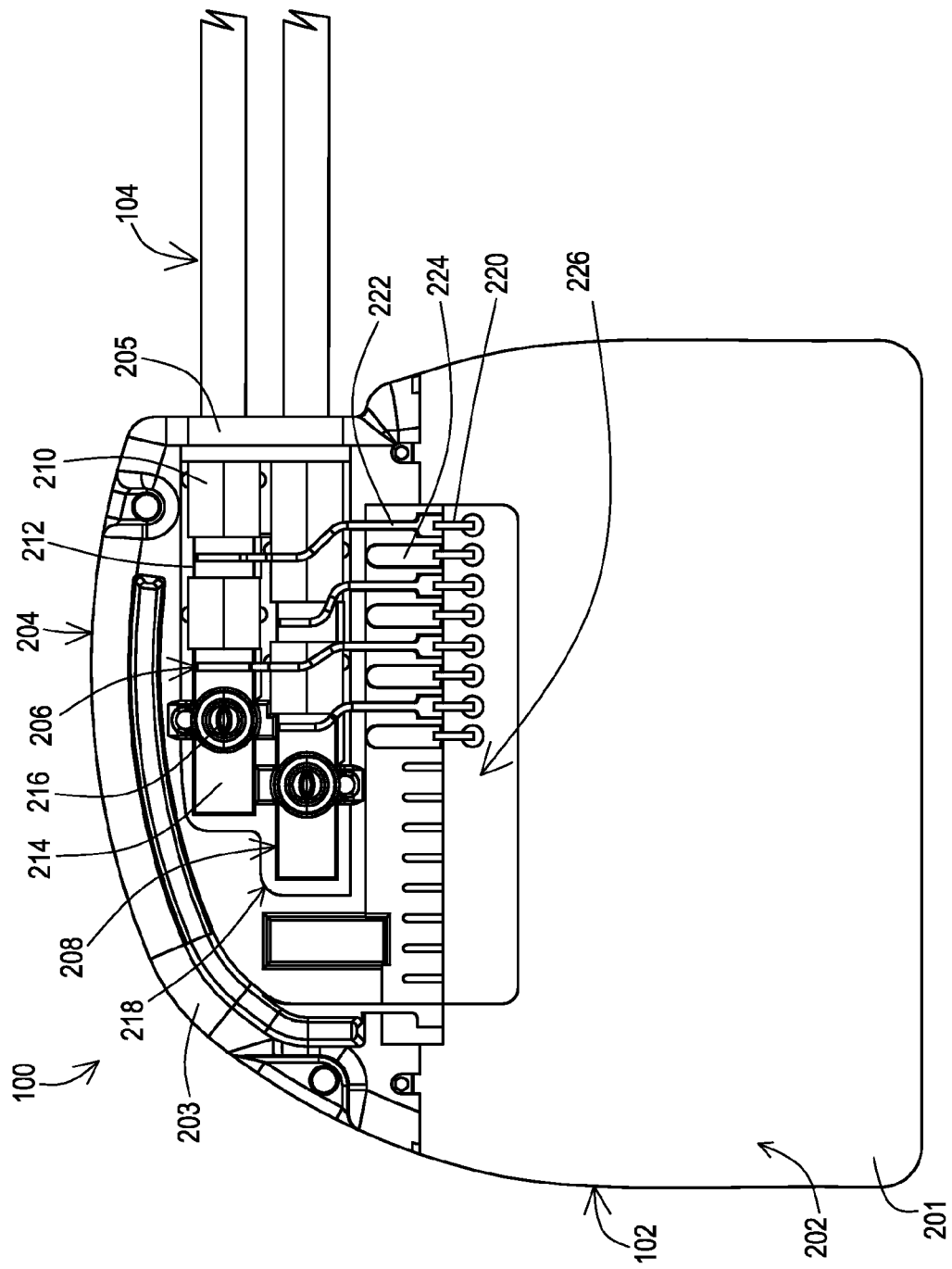
FIG. 2 shows a left side view of an example of an implantable medical device with a medical adhesive filler shown transparently for clarity of illustration.

FIG. 2 shows a side view of the implantable medical device example 102 with medical adhesive that isolates otherwise exposed electrical components shown transparently so that the otherwise exposed electrical components may be clearly viewed. A header structure 204 includes a header body 203 and various internal components mounted within cavities of the header body 203. The cavities of the header body 203 are filled with the medical adhesive that is transparent in FIG. 2 as well as subsequent figures herein. The implantable medical device 102 includes a portion 202 that includes the stimulation and sensing engine, controller, battery, telemetry circuits, and other components that establish the circuitry for performing the medical and communication functions. The portion 202 includes a housing 201 that provides a sealed enclosure for the circuitry contained within the housing. Feedthrough conductors 220 that are connected to the various circuitry within the housing 201 exit the housing 201 in a recessed area 226 that forms a window to the feedthrough conductors 220.

The header structure 204 is mounted atop the portion 202, and specifically atop the housing 201. The feedthrough conductors 220 are electrically coupled to conductive pathways within the header structure 204 that provide an electrical interconnection between each feedthrough conductor 220 and a corresponding electrical connector, such as a Bal Seal® connector, of a stack assembly present within a dedicated and appropriately shaped cavity 218 in the interior of the header structure 204. The cavity 218 is exposed on this side of the header body 203 prior to application of the medical adhesive that covers the cavity 218 and all components therein.

In this example, this side of the medical device 102 includes two vertically spaced stack assemblies 206, 208 within the cavity 218 that share a face 205. The face 205 provides entryways to the lead bores defined by the stack assemblies 206, 208. The electrical connector may be present on this second, or left, side of the medical device 102 that is shown in FIG. 2, such as the electrical connector 212 and a set screw block 214 of stack that acts as an electrical connector in the upper stack assembly 206. Insulative seals 210 are present between each electrical connector of a given stack assembly 206, 208 and between the face 205 and the adjacent electrical connector. A set screw with grommet 216 is present within each set screw block 214.

In this example, a lead frame conductor 222 is provided for each electrical connector, or set screw block acting as an electrical connector, on this side of the medical device 202. The lead frame conductor 222 has one end that acts as a pad for receiving the end of the feedthrough conductor 220, which may be welded or otherwise bonded in an electrically conductive manner to the pad of the lead frame conductor 222.

Figure 3:
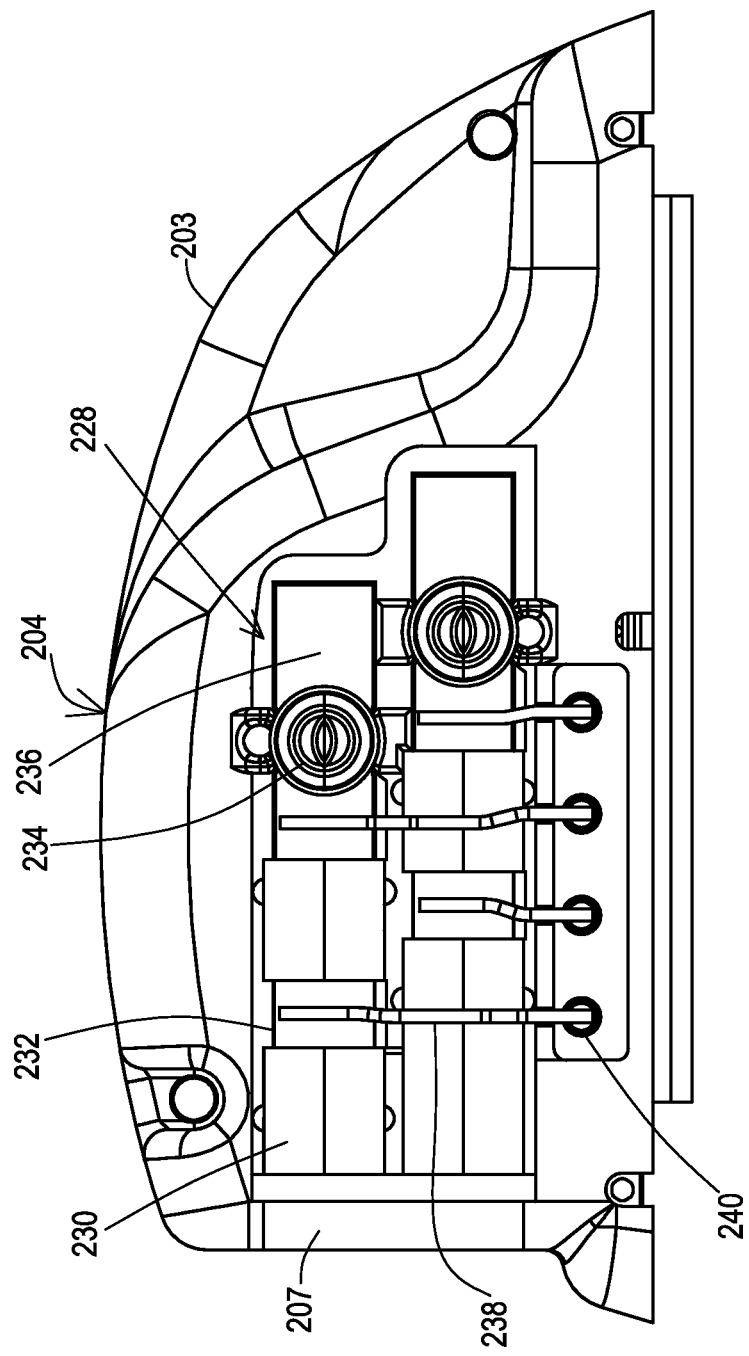
FIG. 3 shows a right side view of an example of a header structure of an implantable medical device with a medical adhesive filler shown transparently for clarity of illustration.

In this example, the feedthrough conductors 220 that are not associated with an electrical conductor of the side of the medical device 102 that is shown in FIG. 2 are instead associated with an electrical connector on a first, or right, side of the medical device 102. Therefore, there is a challenge to establish an electrically conductive pathway from the feedthrough conductor 220 on this side of the medical device 102 to the opposite side of the medical device 102. In this example, there are conductive interconnect pins that pass through corresponding holes from this side shown in FIG. 2, to the other side of the header structure 204 as shown in FIG. 3. The conductive pins are discussed in more detail below with reference to FIGS. 9 and 10. In this example, the end of the conductive interconnect pins includes a tab 224 that is seen in FIG. 2 that extends downward where the end of the feedthrough conductors 220 are attached in an electrically conductive manner to the corresponding tab such as by a weld or other bond.

With reference to FIG. 3, there is an electrically conductive attachment 240 of the conductive pin on this first side of the header structure 204 to a corresponding lead frame conductor 238. The lead frame conductor extends vertically, relative to a horizontal lead bore, to a corresponding electrical connector, such as the electrical connector 232 or a set screw block 236 acting as an electrical connector, to which the lead frame conductor 238 is attached. The electrical conductor 232 and set screw block 236 are part of a stack assembly present within a dedicated and appropriately shaped cavity 228 of the header body 203. The cavity 228 is exposed on this side of the header body 203 prior to application of the medical adhesive that covers the cavity 228 and all components therein.

In this example, this side of the medical device 102 includes two vertically spaced stack assemblies within the cavity 228 that share a face 207. The face 207 provides entryways to the lead bores defined by the stack assemblies. Insulative seals 230 are present between each electrical connector of a given stack assembly and between the face 207 and the adjacent electrical connector 232. A set screw with grommet 234 is present within each set screw block 236.

Figure 4:
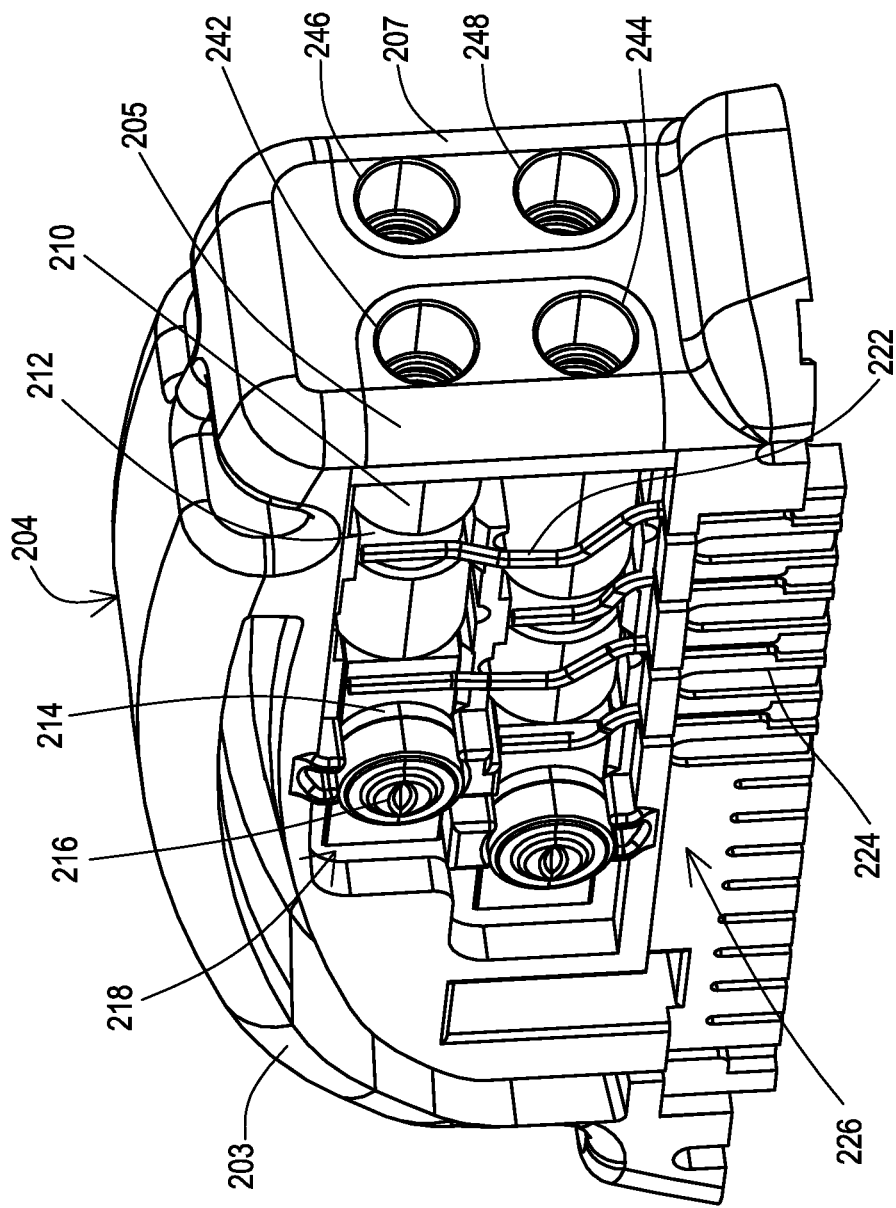
FIG. 4 shows a front left perspective view of the example of the header structure.

FIG. 4 provides a perspective view that illustrates the entryways 242, 244, 246, and 248 within the faces 205 and 207 for the four lead bores of this example. It will be appreciated that any number of lead bores may be provided and that four are shown for purposes of example. It will also be appreciated that any number of electrical connectors per lead bore may be provided and that a single electrical connector with a single set screw block acting as an electrical connector are shown for purposes of example.

Figure 5:
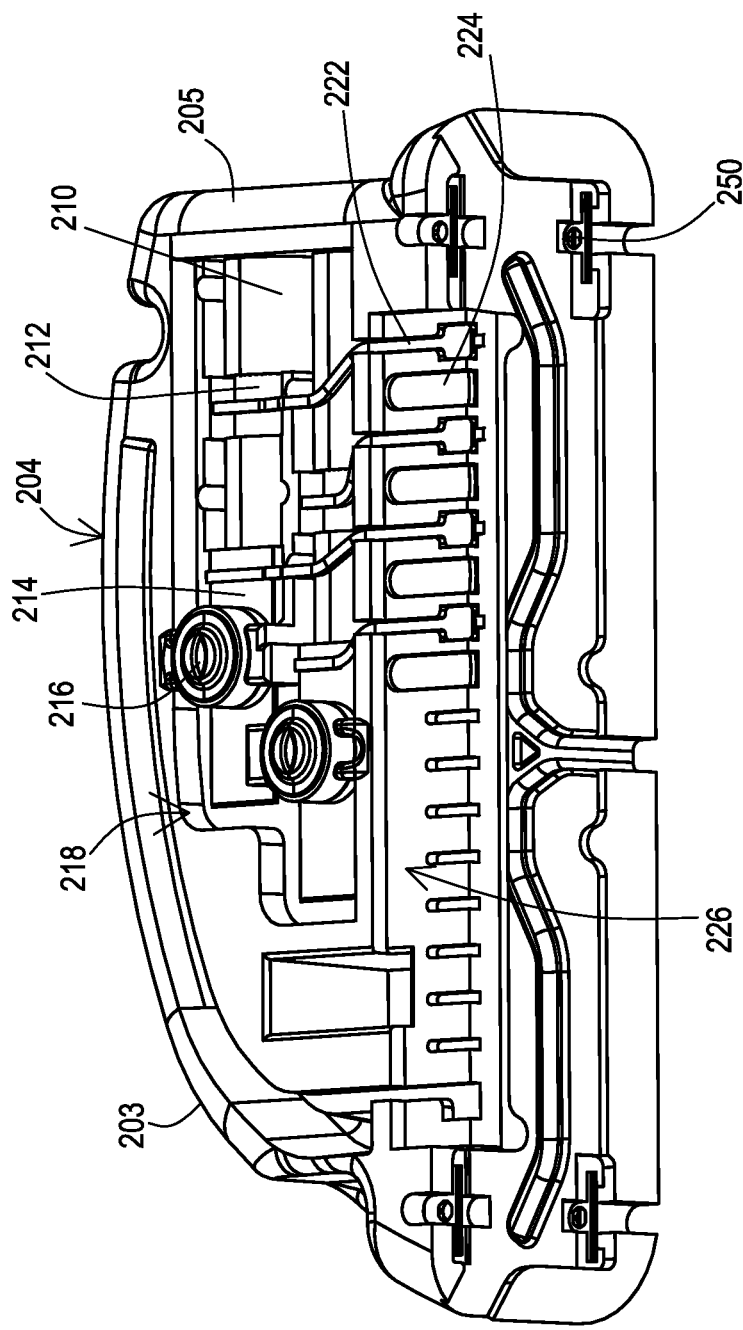
FIG. 5 shows a bottom perspective view of the example of the header structure.

FIG. 5 shows a perspective view that illustrates the bottom of the header structure 204. In particular, tabs 250 can be seen in this view. These tabs 250 are used to attach the header structure 204 to the housing 201 where the housing 201 includes receptacles that receive the tabs 250 to form an interference fit. The separation of the feedthrough conductor window 226 from the cavity 218 can also be seen. As discussed below with reference to FIG. 14, this separation of the feedthrough conductor window 226 from the cavity 218 allows the medical adhesive that fills the cavity 218 and the window 226 to isolate the electrical components and pathways from the external environment to be applied in separate stages.

Figure 6:
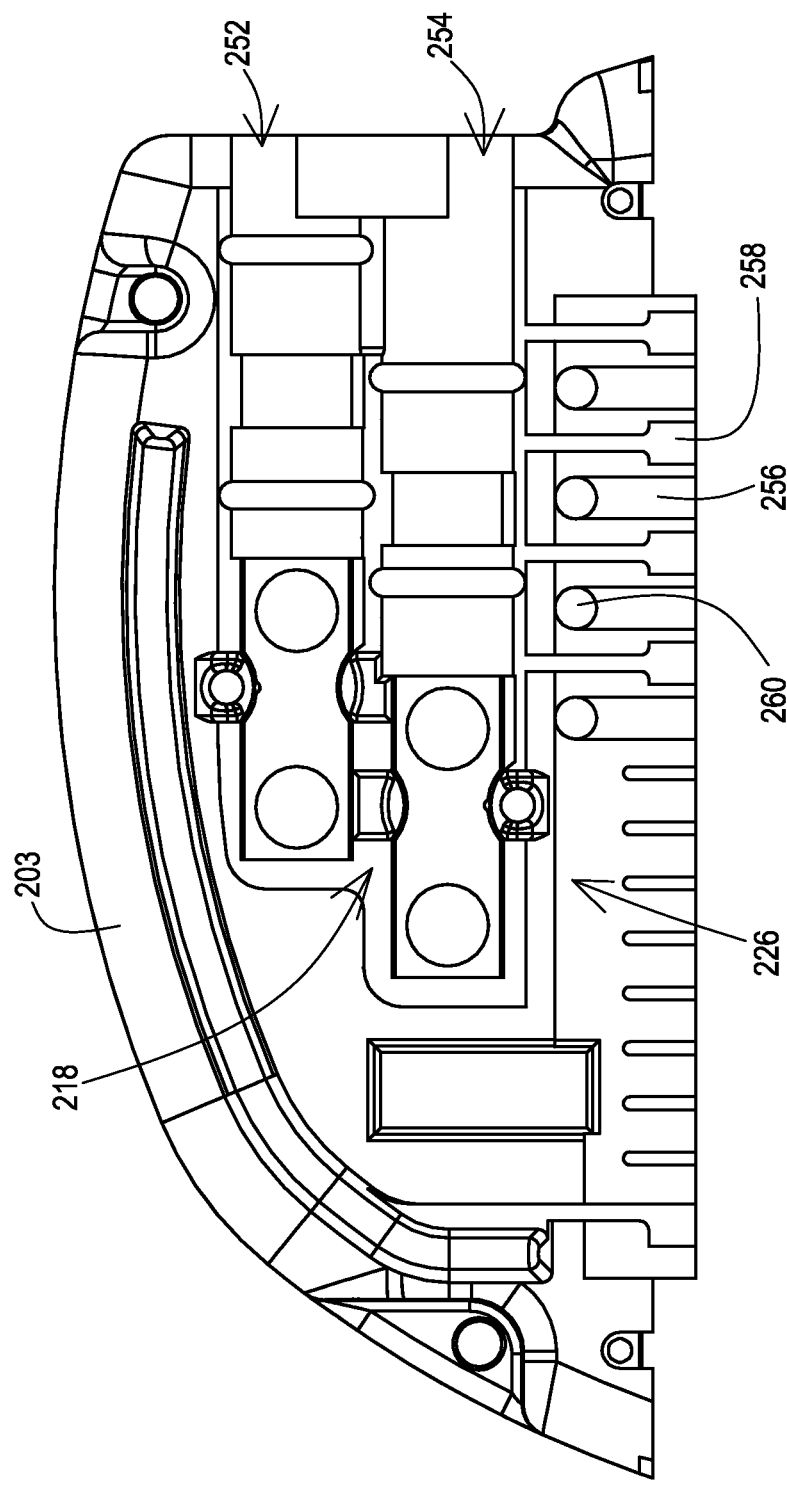
FIG. 6 shows a left side view of the example of a header body of the header structure.
Figure 7:
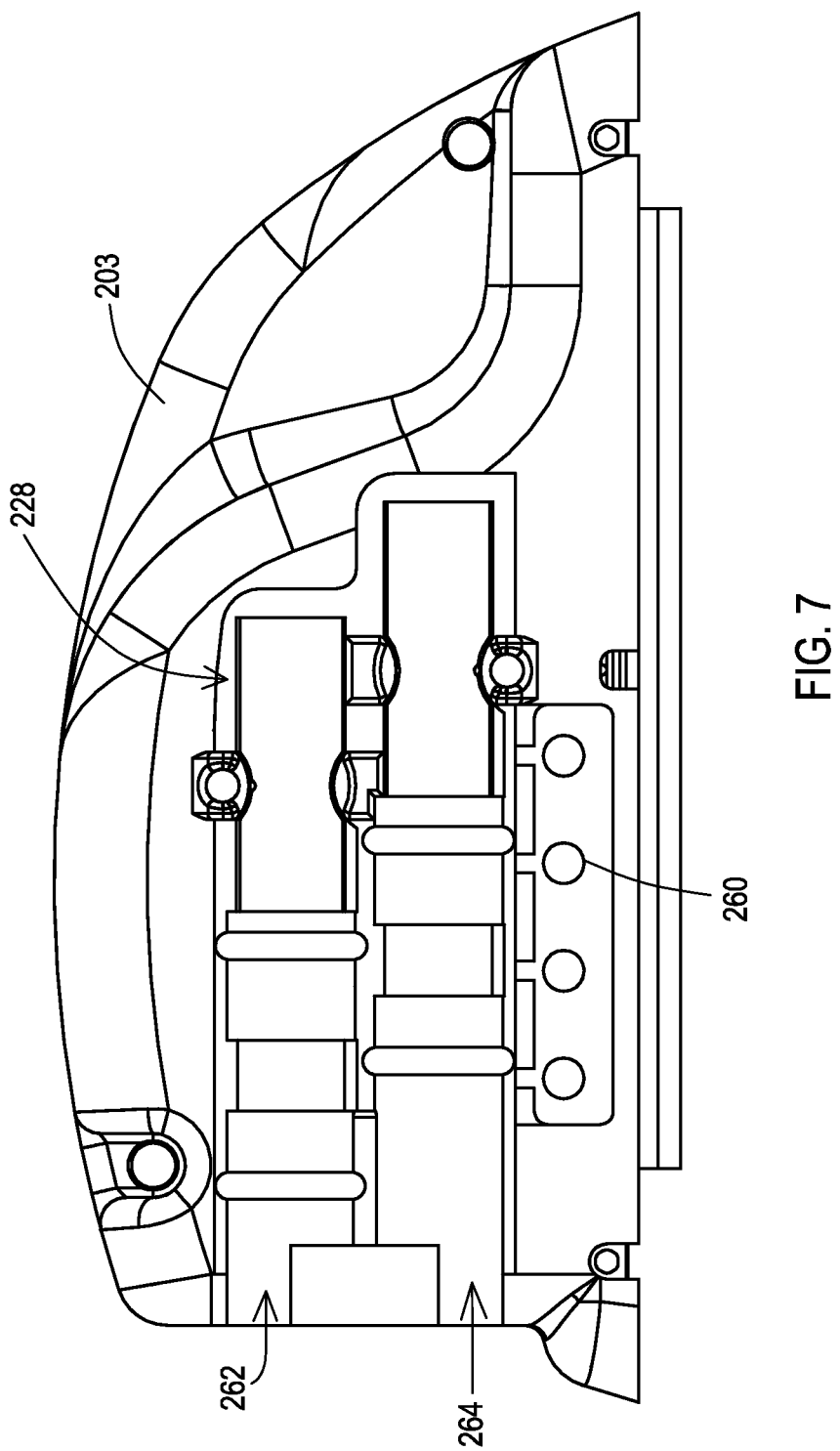
FIG. 7 shows a right side view of the example of a header body of the header structure.
Figure 8:
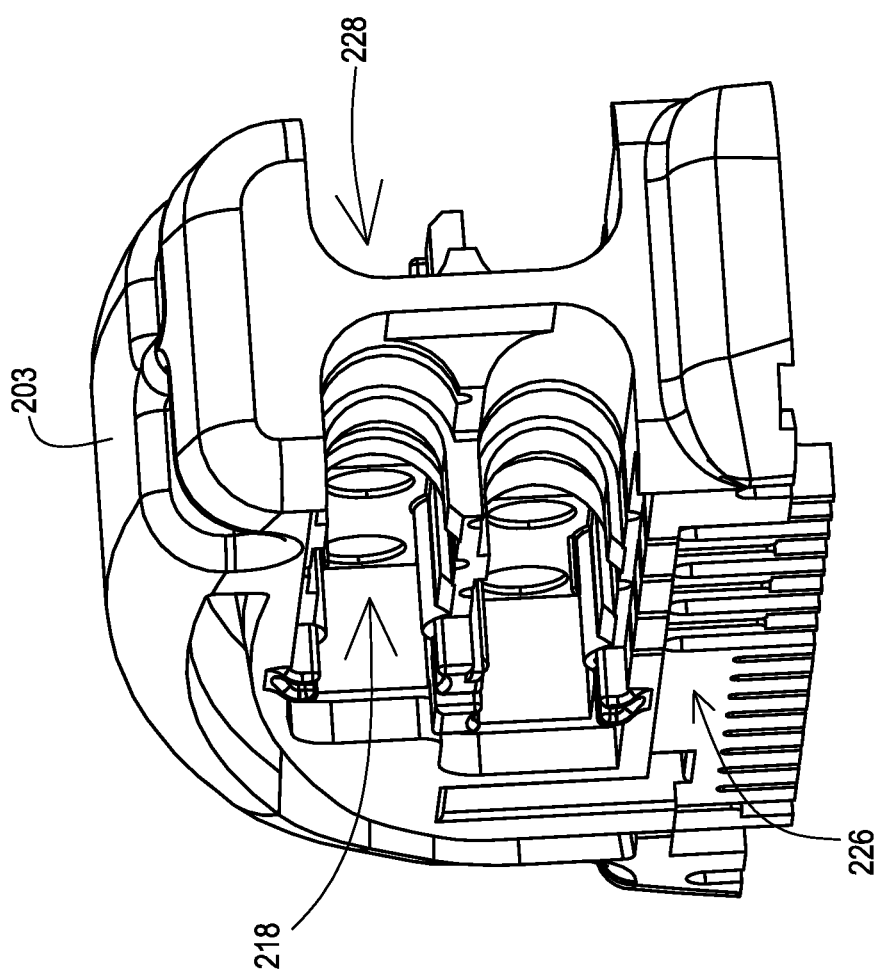
FIG. 8 shows a front perspective view of the example of the header body.

FIGS. 6-8 show views of the header body 203 prior to the installation of any of the electrical components and conductive pathways. With reference to FIG. 6, the header body 203 of this example provides grooves 256 for positioning and isolation of the conductive pin tabs 224 and provides grooves 258 for positioning and isolation of the lead frame conductors 222. FIG. 8 shows the lateral spacing between the cavities 218, 228.

With further reference to FIGS. 6-8, the header body 203 also provides features within the cavity 218 and within the cavity 228 that define the bores 252, 254, 262, and 264 to properly position the electrical connectors, insulative seals, and set screw blocks. Additionally, the header body 203 provides holes 260 that pass from one side to the other side which properly positions and isolates the conductive interconnect pins. In this example, it can be seen from the hole 260 of FIG. 7 and the location of the electrical connectors in FIG. 3 relative to the attachment point 240 which is within the hole 260 of FIG. 7, that each hole 260 is aligned along a horizontal direction with a corresponding electrical connector. This allows the lead frame conductor to travel a simple vertical direction to interconnect the conductive pin within the hole 260 to the electrical connector.

Figure 9:
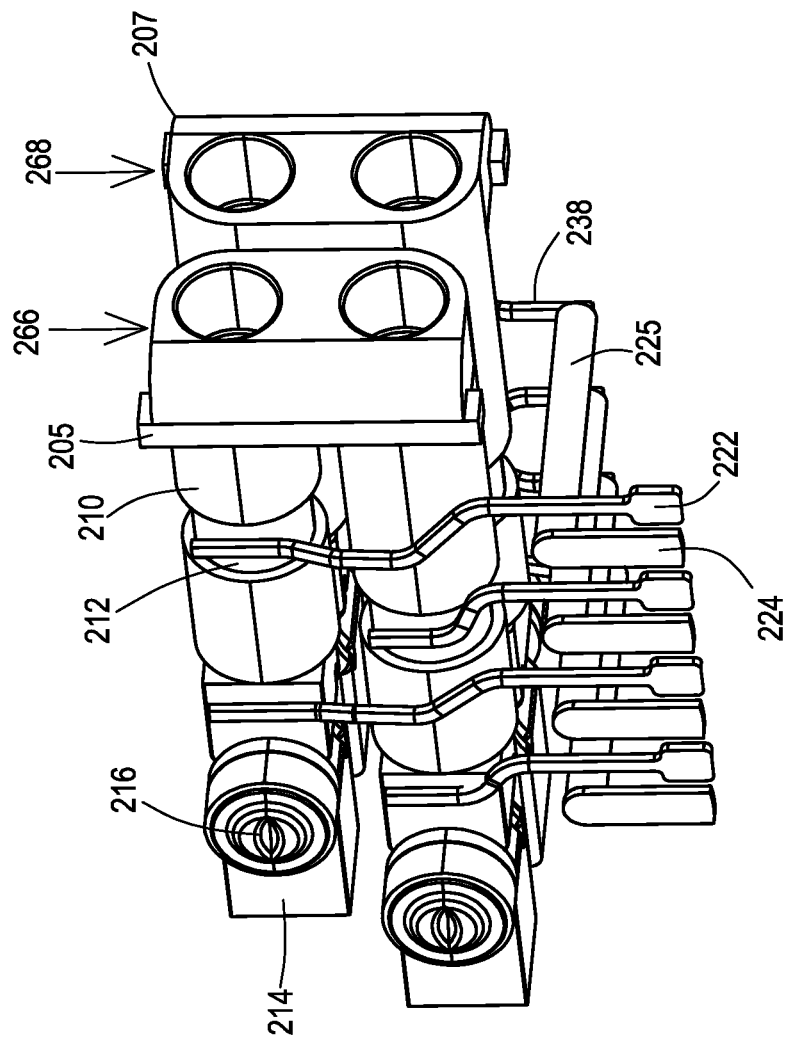
FIG. 9 shows a front left perspective view of stack assemblies of the header structure.
Figure 10:
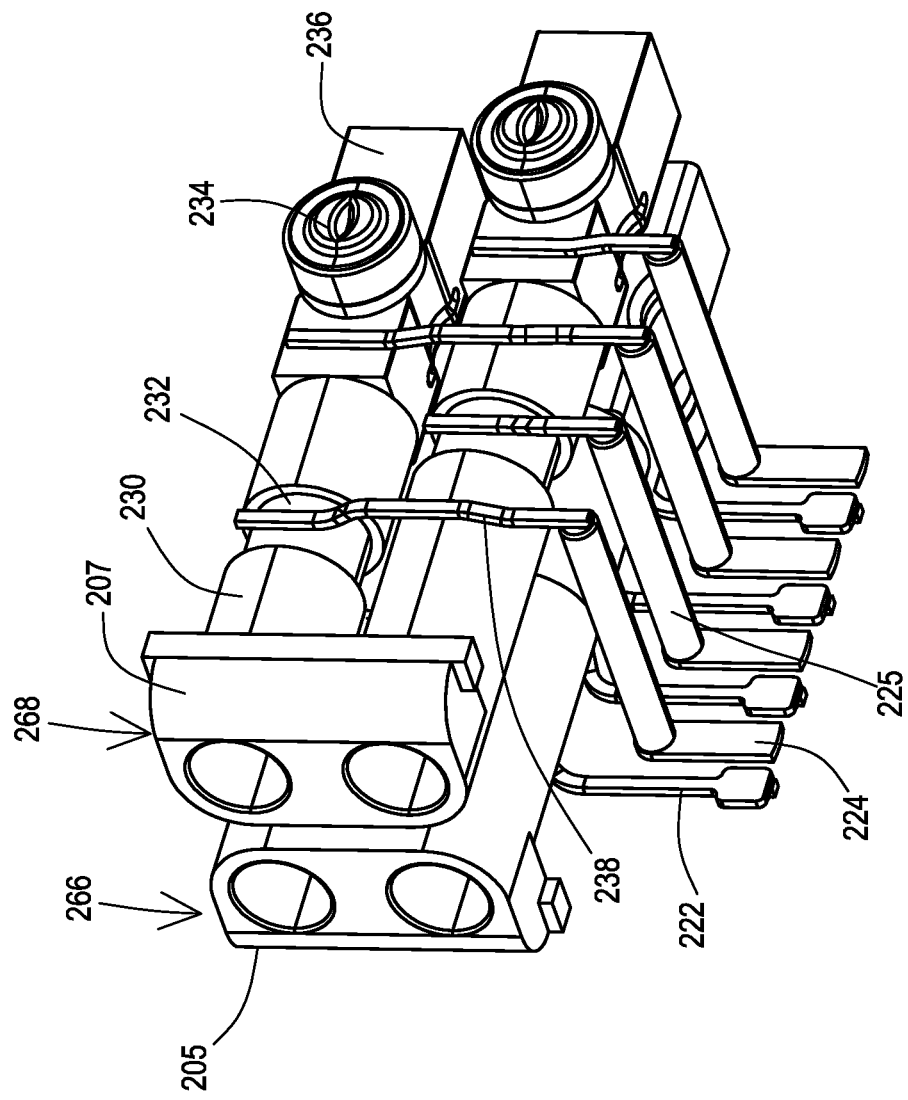
FIG. 10 shows a front right perspective view of stack assemblies of the header structure.

FIGS. 9 and 10 show perspective views of the electrically conductive pathways of the header structure that are established from the feedthrough conductors 220 to the electrical connectors of the stack assemblies. In this example, each side has the two vertically spaced lead bore stack assemblies that are joined by the shared face 205 or 207 to form the two stack duel bore assemblies 266 and 268. The conductive pathway to the first side, which is shown in FIG. 10, from the second side where the feedthrough conductors of the device are exposed, which is shown in FIG. 9, includes the vertical tab 224 which is perpendicular to the remainder of the horizontal conductive pin 225. This conductive path further includes the lead frame conductor 238 which extends from the conductive pin 225 to the corresponding lead frame conductor 238. The horizontal conductive pin 225 is positioned within the corresponding hole 260 of the header body 203 as discussed above with reference to FIG. 6. By having the conductive pins 225 placed within the holes, during construction the lead frame conductors 238 are easily then placed into the cavity 228 as discussed above to complete the conductive path without tedious and problematic manual routing of the conductors from one side of the device to the other and on to the corresponding electrical connector.

Each of the components of the implantable medical device 102 shown in FIGS. 2-10 may be constructed of a variety of materials. For instance the housing 201 may be constructed of biocompatible materials like Titanium. The header body 203 may be constructed of biocompatible materials like Polysulfone. The faces 205, 207 may be constructed of biocompatible materials like Liquid Silicone Rubber. The set screw blocks 214, 236 may be constructed of biocompatible materials like Titanium. The grommets 214, 234 may be constructed of biocompatible materials like Polysulfone. The insulative seals may also be constructed of biocompatible materials like Polysulfone. As discussed above, the electrical connectors may be of various types including Bal Seal® connectors and may be constructed of materials like MP35N® alloys.

Figure 11:
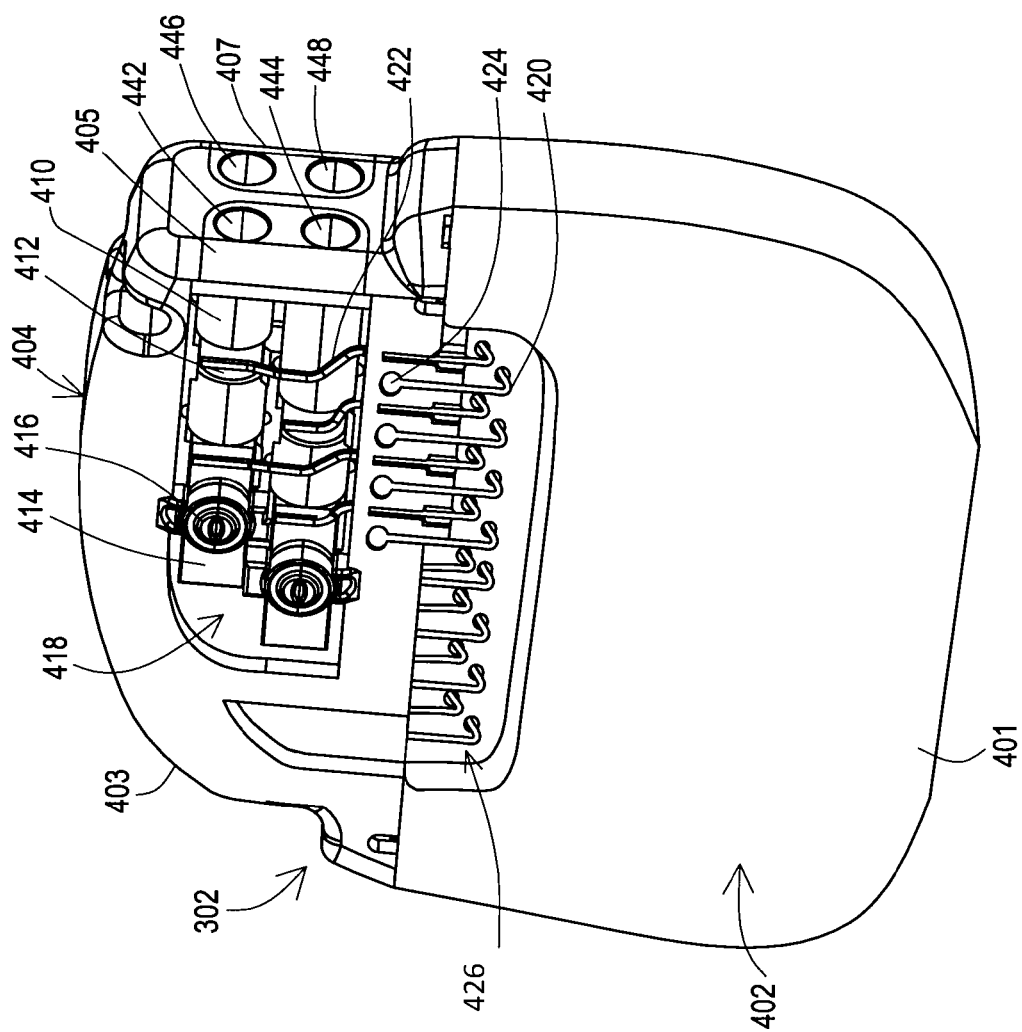
FIG. 11 shows a front left perspective view of a second example of an implantable medical device with a medical adhesive filler shown transparently for clarity of illustration.
Figure 12:
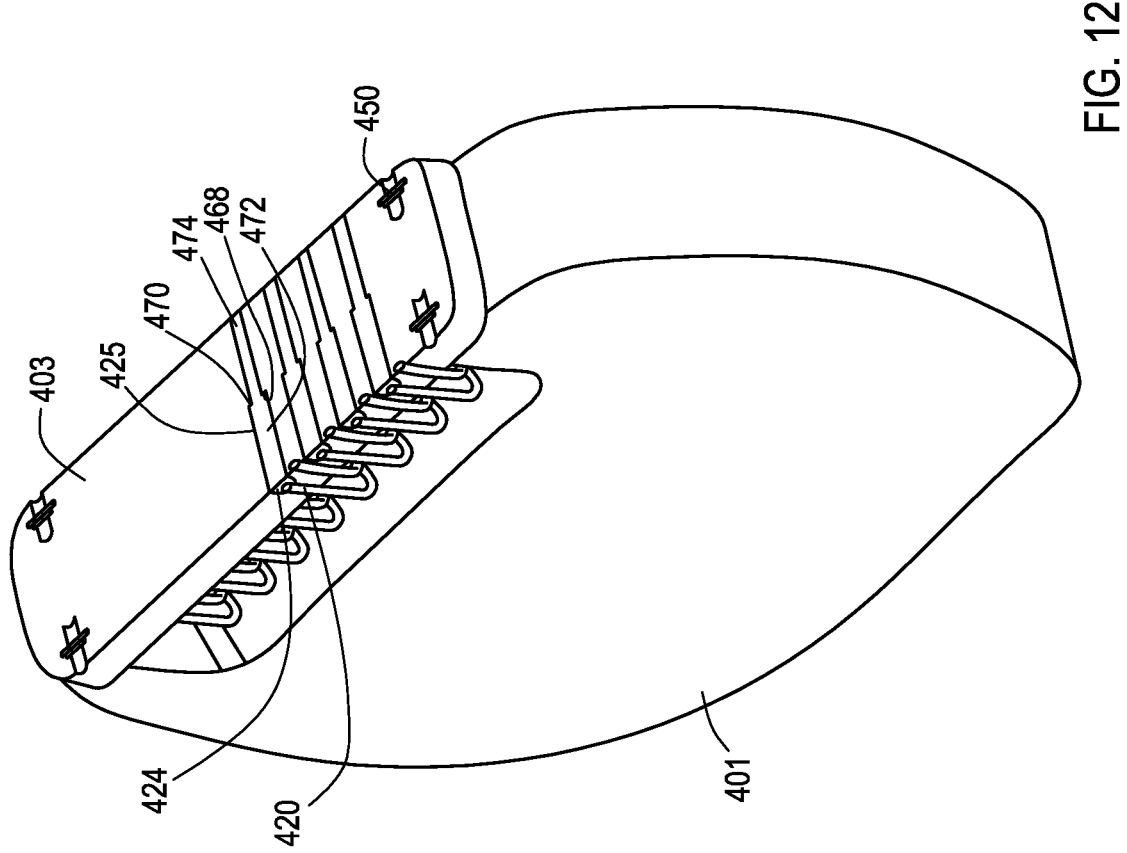
FIG. 12 shows a cross-sectional view taken through a header structure of the second example of the implantable medical device.
Figure 13:
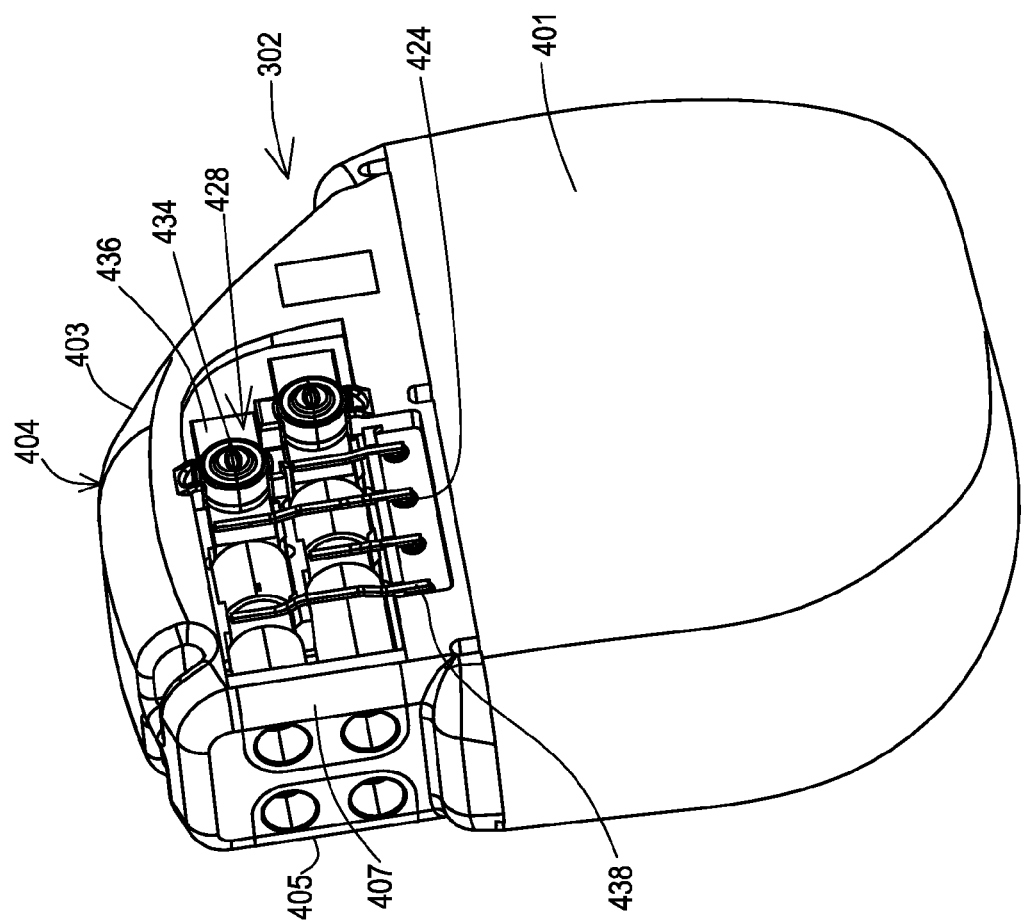
FIG. 13 shows a front right perspective view of the second example of an implantable medical device with a medical adhesive filler shown transparently for clarity of illustration.

FIGS. 11-13 show views of an alternative example of an implantable medical device 302. The implantable medical device example 302 includes a lower portion 402 that includes a housing 401 that houses the electrical circuitry. A header structure 404 is mounted to the housing 401. The header structure 404 includes a header body 403 that includes a cavity 418 on the second, or left, side and a cavity 428 on the first, or right, side. As with the prior example, the cavities 418, 428 hold stack assemblies that include electrical connectors 412, insulative seals 410, set screw blocks 414, 436, and associated set screw grommets 416, and 434. Faces 405 and 407 define the entryways 442, 444, 446, and 448 to the four lead bores of this example. Lead frame conductors 422 and 438 complete the conductive pathway to the electrical connectors. Tabs 450 provide an interference fit to receptacles of the housing 401 and header body 403 to lock the two together. The various components of this alternative example may be constructed of the same types of materials of the like components of the prior example.

In this example, it should be noted that the conductive interconnect pins 424 do not have the vertical tabs of the prior example. However, in this example, the feedthrough conductors 420 which are present within a feedthrough conductor window 426 are trimmed to different lengths depending upon whether a given feedthrough conductor 420 contacts a lead frame conductor 422 or a conductive interconnect pin 424. As shown for the prior example in FIG. 2, those feedthrough conductors 220 are trimmed to the same length.

Another aspect of the example of FIGS. 11-13 that differs from the prior example is best shown in FIG. 12, where a cross-sectional view of the header structure 404 is shown. Here, it can be seen that the conductive interconnect pins 424 include a larger diameter portion 472 and a smaller diameter portion 474. The transition from large diameter to small diameter creates a shoulder 468. Likewise, the hole 425 that the conductive interconnect pin 424 is placed within includes a corresponding larger diameter portion and smaller diameter portion to form a shoulder 470. The shoulder 468 of the pin 424 engages the shoulder 470 of the hole 425 to properly position the pin 424 within the hole 425 which further simplifies the introduction of the conductor pins 424 to the housing body 403 during manufacturing.

Figure 14:
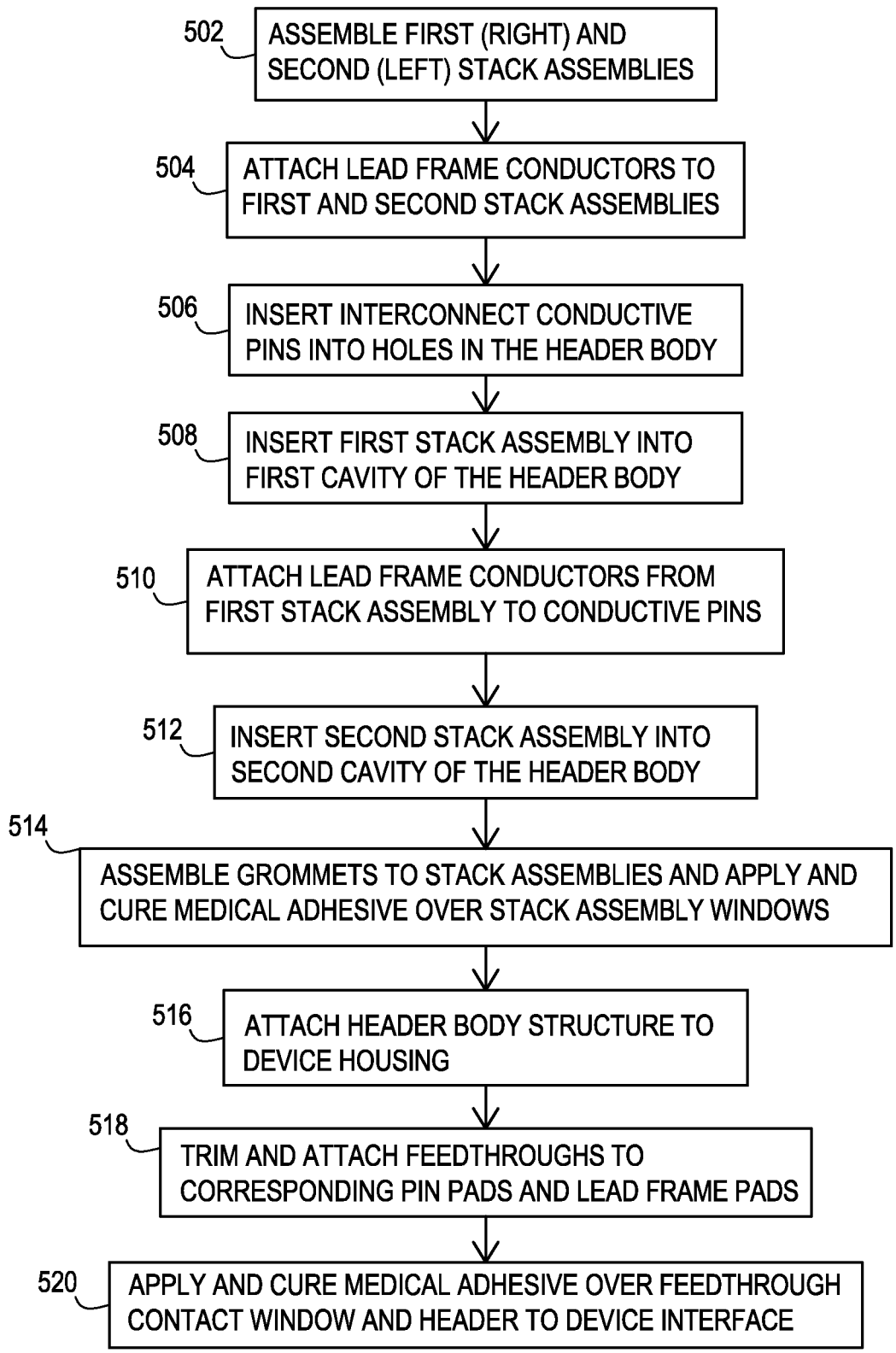
FIG. 14 shows an example of an operational flow for constructing an example of an implantable medical device according to the various embodiments.

FIG. 14 shows an example of a process for constructing an implantable medical device that utilizes the conductive pathway of the header structure from the feedthrough conductor to the electrical connector. In this particular example, the implantable medical device includes left and right stack assemblies providing left and right lead bores. It will be appreciated that the left and right stacks may each include multiple lead bores that are vertically spaced as described above for the examples of FIGS. 2-10. Initially, the first and second stack assemblies are created at an operation 502. This involves placing the set screw block, electrical connectors, and insulative seals of a given stack assembly on a stack pin that holds each of the components in proper alignment. The lead frame conductors may then be attached via a weld or other bond to each electrical connector, as well as to each set screw block acting as an electrical connector, at an operation 504.

To prepare the header body for introduction of the stack assemblies, the conductive interconnect pins may be placed within the holes of the header body that pass from one side to the other at an operation 506. This operation 506 may alternatively be performed prior to either or both of the operations 502, 504. Once the conductive interconnect pins are positioned within the lateral holes of the header body, the first or right side stack assembly may then be placed within the first or right side cavity of the header body at an operation 508. At this point, the lower end of the lead frame conductors of this first stack assembly are positioned at the end of the conductive interconnect pins present within the holes of the header body. The lower end of the lead frame conductors is then attached to the end of the conductive interconnect pin by weld or other bond at an operation 510.

The second or left side stack assembly may be placed within the second or left side cavity of the header body at an operation 512. At this point, the header structure includes all of the internal components and the process proceeds by inserting the grommets for the set screws and then filling the cavities with medical adhesive to cover the stack assemblies within the cavities at an operation 514. The medical adhesive is then allowed to cure, which then effectively isolates the stack assembly components from the external environment. The medical adhesive does not flow into the feedthrough window of the header structure such that the ends of the lead frames and the ends of the conductive pins at the feedthrough window remain exposed. It will be appreciated that the medical adhesive over the stack assemblies may instead be added at a later stage of the process if the stack assemblies are temporarily held in place within the cavities by another technique such as fixturing or retention features within the cavities.

At this point, the header structure that includes the header body and stack assemblies is attached to the housing of the lower portion of the medical device at an operation 516. At this stage, the housing of the medical device already contains the electrical components and the feedthrough conductors are exposed at the top of the housing. As discussed for the embodiments of FIGS. 2-13, tabs may be included to provide an interference fit within receptacles at the bottom of the header body and at the top of the housing to effectively lock the header structure to the housing.

Once the header structure is attached to the housing, the lower end of the lead frame conductors of this first stack assembly are positioned near the exposed end of the feedthrough conductors present at the feedthrough conductor window of the header body. Likewise, the conductive interconnect pins are also positioned near the exposed end of the feedthrough conductors. However, the feedthrough conductors may be longer than necessary to reach the lead frame conductor ends and/or the end of the conductive interconnect pins that is exposed on this second or left side of the header body. Therefore, the feedthrough conductors may be trimmed to size prior to further attachment. Then the lower end of the lead frame conductors which may have a pad shape as well as the exposed end of the conductive interconnect pins, such as the vertical tab 224 of FIG. 2 which may act as a pad, are then attached to the end of the corresponding feedthrough conductor by weld or other electrically conductive bond at an operation 518.

Once the electrical coupling to the feedthrough conductors is complete, the feedthrough window where the attachment to the feedthrough conductors has occurred may then be filled with medical adhesive at an operation 520. The medical adhesive is allowed to cure, and this effectively isolates the feedthrough conductors and the connections to the feedthrough conductors from the external environment. Additionally, if the medical adhesive has not yet been applied over the stack assemblies, the medical adhesive may then be added over the stack assemblies at this stage as well.

Thus, as demonstrated by this process, there is no tedious conductor routing necessary for providing a conductive path from the feedthrough side of the header structure to the electrical connectors of the lead bore on the opposite side. Conductive interconnect pins are easily inserted into the holes while stack assemblies are easily inserted into the cavities on each side of the device that are exposed to the exterior prior to being filled with the medical adhesive.

While embodiments have been particularly shown and described, it will be understood by those skilled in the art that various other changes in the form and details may be made therein without departing from the spirit and scope of the invention.

What is claimed is:

1. An implantable medical device, comprising:
   a housing;
   a plurality of feedthrough conductors that exit the housing;
   a header structure having a plurality of holes passing from a first side of the header structure to a second side of the header structure;
   a plurality of conductive pins, with a conductive pin of the plurality present within a corresponding hole of the plurality of holes, the conductive pin having a first end present on the first side of the header structure and a second end present on the second side of the header structure, the second end being electrically coupled to a corresponding feedthrough conductor of the plurality of feedthrough conductors;
   electrical connectors present within an interior of the header structure; and
   a first set of lead frame conductors with each lead frame conductor of the first set being electrically coupled to the first end of a corresponding conductive pin of the plurality of conductive pins present within one of the holes and being electrically coupled to a corresponding electrical connector within the header structure.

2. The implantable medical device of claim 1, further comprising a second set of lead frame conductors with each lead frame conductor of the second set being electrically coupled to a corresponding feedthrough conductor of the plurality of feedthrough conductors, the second set of conductors also being electrically coupled to a corresponding electrical connector present within the header structure.

3. The implantable medical device of claim 2, wherein the header structure comprises a header body with a first cavity exposed to the first side of the header body and a second cavity exposed to the second side of the header body, with a first set of the electrical connectors that are electrically coupled to the first set of lead frame conductors being present within the first cavity and with a second set of the electrical connectors that are electrically coupled to the second set of lead frame conductors being present within the second cavity.

4. The implantable medical device of claim 3, wherein the electrical connectors within the first cavity form two bores and wherein the electrical connectors within the second cavity form two bores.

5. The implantable medical device of claim 1, wherein each hole of the plurality of holes of the header structure defines a shoulder, wherein each of the conductive pins defines a shoulder, and wherein the shoulder of each conductive pin engages the shoulder of a corresponding hole of the plurality of holes.

6. The implantable medical device of claim 1, wherein each of the conductive pins includes a tab that extends from the second end of the conductive pin perpendicularly relative to the portion of the conductive pin that extends between the first and second sides.

7. The implantable medical device of claim 1, wherein each lead frame conductor travels in a vertical direction from the conductive pin to the connector, with each hole being aligned along a horizontal direction with a corresponding electrical connector.

* * * * *